United States Patent
Shaw

(10) Patent No.: US 9,254,308 B2
(45) Date of Patent: Feb. 9, 2016

(54) KITS AND METHODS FOR THE TREATMENT OF CANCER USING GLIADIN PEPTIDES

(71) Applicant: BARMARSA RESEARCH LLC, Inverness, IL (US)

(72) Inventor: Fred L. Shaw, Inverness, IL (US)

(73) Assignee: BARMARSA RESEARCH LLC, Inverness, IL (US)

( * ) Notice: Subject to any disclaimer, the term of this patent is extended or adjusted under 35 U.S.C. 154(b) by 0 days.

(21) Appl. No.: 14/200,585

(22) Filed: Mar. 7, 2014

(65) Prior Publication Data
US 2014/0256647 A1 Sep. 11, 2014

Related U.S. Application Data

(60) Provisional application No. 61/774,285, filed on Mar. 7, 2013.

(51) Int. Cl.

| | | |
|---|---|---|
| *A61K 36/899* | (2006.01) | |
| *A61K 31/282* | (2006.01) | |
| *A61K 31/517* | (2006.01) | |
| *A61K 35/74* | (2015.01) | |
| *A61K 38/16* | (2006.01) | |
| *A61B 6/00* | (2006.01) | |
| *A61P 35/00* | (2006.01) | |
| *B82Y 5/00* | (2011.01) | |
| *A61K 38/10* | (2006.01) | |
| *A61K 45/06* | (2006.01) | |
| *A61K 35/744* | (2015.01) | |
| *A61K 31/513* | (2006.01) | |
| *A61K 31/5377* | (2006.01) | |
| *A61K 33/24* | (2006.01) | |

(52) U.S. Cl.
CPC .............. *A61K 38/10* (2013.01); *A61K 31/513* (2013.01); *A61K 31/517* (2013.01); *A61K 31/5377* (2013.01); *A61K 33/24* (2013.01); *A61K 35/744* (2013.01); *A61K 36/899* (2013.01); *A61K 38/168* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 6,045,809 A | * | 4/2000 | Postaire et al. ............... | 424/400 |
| 2003/0171318 A1 | | 9/2003 | Morham et al. | |
| 2004/0105851 A1 | * | 6/2004 | Okada et al. ................. | 424/94.4 |

FOREIGN PATENT DOCUMENTS

| | | |
|---|---|---|
| WO | WO-2005/021757 A1 | 3/2005 |
| WO | WO-2012/031027 A1 | 3/2012 |
| WO | WO-2014/002108 A1 | 1/2014 |

OTHER PUBLICATIONS

UniprotKB/Swiss-Prot Accession No. E7DRK7 (accessed Nov. 7, 2014 at URL: uniprot.org/uniprot/E7DRK7).*
Tan et al., "Anti-cancer natural products isolated from Chinese medicinal herbs," Chinese Med. 6:27-42 (2011).*
Gulfam et al., "Anticancer drug-loaded gliadin nanoparticles induce apoptosis in breast cancer cells," Langmuir 28:8216-8223 (May 8, 2012).*
Sharma et al., "Receptor Tryosine Kinase Inhibitors as Potent Weapons in War Against Cancers," Curr. Pharma. Design 15:758-776 (2009).*
Overview of Leukemia at URL merckmanuals.com/home/blood_disorders/leukemias/overview_of_leukemia.html?qt=Leukemia&alt=sh accessed Aug. 20, 2014).*
National Institute of Cancer—understanding and related topics, accessed Aug. 21, 2014 at URL: cancer.gov/cancertopics/understandingcancer.*
Merck Manuals Brain Tumors accessed Aug. 21, 2014 at URL merckmanuals.com/home/brain_spinal_cord_and_nerve_disorders/tumors_of_the_nervous_system/brain_tumors.html).*
Merck Manual Colorectal Cancer accessed Aug. 21, 2014 at URL merckmanuals.com/home/digestive_disorders/tumors_of_the_digestive_system/colorectal_cancer.html).*
Merck Manual Breast Cancer accessed Aug. 21, 2014 at URL: merckmanuals.com/home/womens_health_issues/breast_disorders/breast_cancer.html).*
Merck Manual Prostate Cancer accessed Aug. 21, 2014 at URL: merckmanuals.com/home/kidney_and_urinary_tract_disorders/cancers_of_the_kidney_and_genitourinary_tract/prostate_cancer.html?qt=prostate cancer&alt=sh.*
Ovarian Cancer, accessed Aug. 21, 2014 at merckmanuals.com/home/womens_health_issues/cancers_of_the_female_reproductive_system/ovarian_cancer.html?qt=ovarian cancer&alt=sh.*
Merck Manual Bladder Cancer accessed Aug. 21, 2014 at URL: merckmanuals.com/home/kidney_and_urinary_tract_disorders/cancers_of_the_kidney_and_genitourinary_tract/bladder_cancer.html.*

(Continued)

*Primary Examiner* — Julie Ha
*Assistant Examiner* — Kristina M Hellman
(74) *Attorney, Agent, or Firm* — Marshall, Gerstein & Borun LLP

(57) ABSTRACT

Kits and methods for treating cancer comprising administration of a gliadin peptide to a patient are disclosed herein. A kit according to the invention comprises a pharmaceutical composition comprising a gliadin peptide and instructions for administering the peptide to a patient. The kit may further comprise a pharmaceutical composition comprising at least one chemotherapeutic agent such as a receptor tyrosine kinase inhibitor and instructions for co-administering the compounds. A method of treating cancer according to the invention comprises administering a gliadin peptide to a patient and may further comprise co-administering at least one chemotherapeutic agent such as a receptor tyrosine kinase inhibitor. Co-administration of a gliadin peptide and receptor tyrosine kinase inhibitor to a patient with cancer is effective to decrease or prevent resistance of the cancer to the receptor tyrosine kinase inhibitor.

15 Claims, No Drawings

(56) References Cited

OTHER PUBLICATIONS

Merck Manual Cancer of the Uterus, accessed Aug. 21, 2014 at URL: merckmanuals.com/home/womens_health_issues/cancers_of_the_female_reproductive_system/cancer_of_the_uterus.html?qt=Cancer of the Uterus&alt=sh.*
Duester, "Retinoic Acid Synthesis and Signaling during Early Organogenesis," Cell 134:921-931 (2008).*
Elli et al., "Gliadin cytotoxicity and in vitro cell cultures," Toxicol. Lett. 146:1-8 (2003).*
Ciccocioppo et al., "The immune recognition of gluten in coeliac disease," Clin. Exp. Immunol. 140:408-416 (2005).*
Arora et al., Role of tyrosine kinase inhibitors in cancer therapy, J. Pharmacol. Exp. Ther., 315(3):971-9 (2005).
Auricchio et al., Dietary proteins and mechanisms of gastrointestinal diseases: gliadin as a model, J. Pediatr. Gastroenterol. Nutr., 39:S738-9 (2004).
Auricchio et al., Effects of gliadin-derived peptides from bread and durum wheats on small intestine cultures from rat fetus and coeliac children, Pediatr. Res., 16:1004-10 (1982).
Barone et al., Gliadin peptide P31-43 localises to endocytic vesicles and interferes with their maturation, PLoS One, 5(8):e12246 (2010).
Barone et al., Growth factor-like activity of gliadin, an alimentary protein: implications for coeliac disease, Gut, 56:480-8 (2007).
Bethune et al., Parallels between pathogens and gluten peptides in celiac sprue, PLoS Pathogens, 4(2):e34 (2008).
Blazek et al., The Cyclin K/Cdk12 complex maintains genomic stability via regulation of expression of DNA damage response genes, Genes Dev., 25:2158-72 (2011).
Blazek, The cyclin K/Cdk12 complex: an emerging new player in the maintenance of genome stability, Cell Cycle, 11:6, 1049-50 (2012).
Bokobza et al., Short-course treatment with gefitinib enhances curative potential of radiation therapy in a mouse model of human non-small cell lung cancer, Int. J. Radiation Oncol. Biol. Phys., 88(4):947-54 (2014).
Bryant et al., EGF induces macropinocytosis and SNX1-modulated recycling of E-cadherin, J. Cell Sci., 120:1818-28 (2007).
Buck et al., Loss of homotypic cell adhesion by epithelial-mesenchymal transition or mutation limits sensitivity to epidermal growth factor receptor inhibition, Mol. Cancer Ther., 6(2):532-41 (2007).
Busse et al., Reversible G(1) arrest induced by inhibition of the epidermal growth factor receptor tyrosine kinase requires up-regulation of p27(KIP1) independent of MAPK activity, J. Biol. Chem., 275(10):6987-95 (2000).
Byers et al., An epithelial-mesenchymal transition gene signature predicts resistance to EGFR and PI3K inhibitors and identifies axl as a therapeutic target for overcoming EGFR inhibitor resistance, Clin. Cancer Res., 19(1):1-12 (2012).
Caputo et al., Gliadin Peptides Induce Tissue Transglutaminase Activation and ER-Stress through Ca2+ Mobilization in Caco-2 Cells, PLoS One, 7(9): e45209 (2012).
Ciccocioppo et al., The immune recognition of gluten in coeliac disease, Clin. Exp. Immunol., 140:408-16 (2005).
Cohen et al., United States Food and Drug Administration Drug Approval Summary—Gefitinib (ZD1839 Iressa) Tablets, Clin. Cancer Res., 10:1212-8 (2004).
Cornell et al., Amino acid composition of gliadin fractions which may be toxic to individuals with coeliac disease, Clinica Chimica Acta, 123:311-9 (1982).
Cornell et al., Intestinal mucosa of celiacs in remission is unable to abolish toxicity of gliadin peptides on in Vitro developing fetal rat intestine and cultured atrophic celiac mucosa, Pediatric Res., 24(2):233-7 (1988).
Cyclin-dependent kinase 12—Homo sapiens (Human), downloaded from the Internet at: <http://www.uniprot.org/uniprot/Q9NYV4> (last modified May 14, 2014).
Cyclin-K-Homo sapiens (Human), downloaded from the Internet at: <http://www.uniprot.org/uniprot/O75909> (last modified May 14, 2014).
Dai et al., Cyclin K-containing kinase complexes maintain self-renewal in murine embryonic stem cells, J. Biol. Chem., 287(30):25344-52 (2012).
Das et al., Somatic mutations in the tyrosine kinase domain of epidermal growth factor receptor (EGFR) abrogate EGFR-mediated radioprotection in non-small cell lung carcinoma, Cancer Res., 67:5267-74 (2007).
De Ritis et al., Toxicity of wheat flour proteins and protein-derived peptides for in vitro developing intestine from rat fetus, Pediat. Res., 13:1255-61 (1979).
Dolfini et al., In vitro cytotoxic effect of bread wheat gliadin on the LoVo human adenocarcinoma cell line, Toxicology in Vitro, 16(4):331-7 (2002).
Dupont et al., Deciphering the complexities of the wheat flour proteome using quantitative two-dimensional electrophoresis, three proteases and tandem mass spectrometry, Proteome Sci., 9:10 (2011).
Ebos et al., Accelerated metastasis after short-term treatment with a potent inhibitor of tumor angiogenesis, Cancer Cell, 15:232-9 (2009).
Favoni et al., Gefitinib targets EGFR dimerization and ERK1-2 phosphorylation to inhibit pleural mesothelioma cell proliferation, Curr. Cancer Drug Targets, 10:176-91 (2010).
Fidler et al., The Potential Predictive Value of Cyclooxygenase-2 Expression and Increased Risk of Gastrointestinal Hemorrhage in Advanced Non-Small Cell Lung Cancer Patients Treated with Erlotinib and Celecoxib, Clin. Cancer Res., 14:2088-94 (2008).
Frederick et al., Epithelial to mesenchymal transition predicts gefitinib resistance in cell lines of head and neck squamous cell carcinoma and non-small cell lung carcinoma, Mol. Cancer Ther., 6(6):1683-91 (2007).
Freeman et al., Tumor penetration and epidermal growth factor receptor saturation by panitumumab correlate with antitumor activity in a preclinical model of human cancer, Mol. Cancer, 11:47 (2012).
Furukawa et al., Gefitinib-sensitive EGFR lacking residues 746-750 exhibits hypophosphorylation at tyrosine residue 1045, hypoubiquitination, and impaired endocytosis, DNA and Cell Biol., 26(3):178-85 (2007).
Gasbarrini et al., Recurrent spontaneous abortion and intrauterine fetal growth retardation as symptoms of coeliac disease, The Lancet, 356:399-400 (2000).
Gazdar, Activating and resistance mutations of EGFR in non-small-cell lung cancer: role in clinical response to EGFR tyrosine kinase inhibitors, Oncogene, 28(Suppl 1):S24-31 (2009).
Giovannini et al., Induction of apoptosis in Caco-2 cells by wheat gliadin peptides, Toxicology, 145:63-71 (2000).
Giovannini et al., Wheat gliadin induces apoptosis of intestinal cells via an autocrine mechanism involving Fas-Fas ligand pathway, FEBS Lett., 540:117-24 (2003).
Golpon et al., Life after corpse engulfment—phagocytosis of apoptotic cells leads to VEGF secretion and cell growth, The FASEB J., 28 pp. (2004).
Gottschling et al., The gefitinib long-term responder (LTR)—a cancer stem-like cell story? Insights from molecular analyses of German long-term responders treated in the IRESSA expanded access program (EAP), Lung Cancer, 77(1):183-91 (2012).
Gulfam et al., Anticancer drug-loaded gliadin nanoparticles induce apoptosis in breast cancer cells, Langmuir, 28(21):8216-23 (2012).
Guo et al., Signaling networks assembled by oncogenic EGFR and c-Met, PNAS, 105(2):692-7 (2008).
Hause et al., Comprehensive binary interaction mapping of SH2 domains via fluorescence polarization reveals novel functional diversification of ErbB receptors, PLoS One, 7(9):e44471 (2012).
Henne et al., The ESCRT pathway, Dev. Cell, 21(1):77-91 (2011).
Hotta et al., Gefitinib induces premature senescence in non-small cell lung cancer cells with or without EGFR gene mutation, Oncol. Reports, 17:313-7 (2007).
Hudson et al., Non-specific cytotoxicity of wheat gliadin components towards cultured human cells, The Lancet, pp. 339-341 (1976).
Huether et al., Erlotinib induces cell cycle arrest and apoptosis in hepatocellular cancer cells and enhances chemosensitivity towards cytostatics, J. Hepatology, 43:661-9 (2005).

(56) References Cited

OTHER PUBLICATIONS

Hurley et al., The ESCRT Complexes—Structure and Mechanism of a Membrane-Trafficking Network, Annu. Rev. Biophys. Biomol. Struct., 35:277-98 (2006).
Iacomino et al., Structural analysis and Caco-2 cell permeability of the celiac-toxic A-gliadin peptide 31-55, J. Agric. Food Chem., 33 pp. (Jan. 8, 2013).
International Search Report and Written Opinion, corresponding International Application No. PCT/US2014/021660, mailing date Jun. 27, 2014.
Khan et al., Cyclin K inhibits HIV-1 gene expression and replication by interfering with cyclin-dependent kinase 9 (CDK9)-cyclin T1 interaction in nef-dependent manner, J. Biol. Chem., 286:22943-54 (2011).
Ko et al., CrkRS: a novel conserved Cdc2-related protein kinase that colocalises with SC35 speckles, J. Cell Sci., 114(14):2591-603 (2001).
Koyama et al., ZD1839 induces p15INK4b and causes G1 arrest by inhibiting the mitogen-activated protein kinase-extracellular signal-regulated kinase pathway, Mol. Cancer Ther., 6:1579-87 (2007).
Krall et al., High- and Low-Affinity Epidermal Growth Factor Receptor-Ligand Interactions Activate Distinct Signaling Pathways, PLoS One, 6(1):e15945 (2011).
Lamagna et al., Dual role of macrophages in tumor growth and angiogenesis, J. Leukoc. Biol., 80:705-13 (2006).
Li et al., A study on the long-term non-small cell lung cancer survivors in the expand access program of gefitinib in China, Chin. J. Lung Cancer, 15(6):332-9 (2012).
Lin et al., Evidence showing that a proline-specific endopeptidase has an absolute requirement for a trans peptide bond immediately preceding the active bond, Biochemistry, 22(19):4480-5 (1983).
Lindfors et al., Live probiotic Bifidobacterium lactis bacteria inhibit the toxic effects induced by wheat gliadin in epithelial cell culture, Clin. Exp. Immunol., 152:552-8 (2008).
Ling et al., Erlotinib Induces p27KIP1 Up-Regulation and Nuclear Translocation in Association with Cell Growth Inhibition and G1-S Phase Arrest in Human Non-Small-Cell Lung Cancer Cell Lines, Mol. Pharm., 72(2):248-58 (2007).
Luciani et al., Lysosomal accumulation of gliadin p31-43 peptide induces oxidative stress and tissue transglutaminase-mediated PPARgamma downregulation in intestinal epithelial cells and coeliac mucosa, Gut, 59:311-9 (2010).
Ludvigsson et al., Celiac disease and risk of adverse fetal outcome: a population-based cohort study, Gastroenterology, 129:454-63 (2005).
Ludvigsson et al., Reduced risk of breast, endometrial and ovarian cancer in women with celiac disease, Int. J. Cancer, 131:E244-50 (2012).
Lundquist et al., Kaposi sarcoma-associated viral cyclin K overrides cell growth inhibition mediated by oncostatin M through STAT3 inhibition, Blood, 101:4070-7 (2003).
Martinelli et al., Coeliac disease and unfavourable outcome of pregnancy, Gut, 46:332-5 (2000).
Matysiak-Budnik et al., Alterations of the intestinal transport and processing of gliadin peptides in celiac disease, Gastroenterology, 125(3):696-707 (2003).
Mima et al., Epithelial-mesenchymal transition expression profiles as a prognostic factor for disease-free survival in hepatocellular carcinoma—Clinical significance of transforming growth factor-? signaling, Oncol. Lett., 5:149-54 (2013).
Mink et al., Cancer-associated fibroblasts derived from EGFR-TKI-resistant tumors reverse EGFR pathway inhibition by EGFR-TIKs, Mol. Cancer Res., 8:809-20 (2010).
Nakajima et al., N-Cadherin Expression and Epithelial-Mesenchymal Transition in Pancreatic Carcinoma, Clin. Cancer Res., 10:4125-33 (2004).
Naumov et al., Combined vascular endothelial growth factor receptor and epidermal growth factor receptor (EGFR) blockade inhibits tumor growth in xenograft models of EGFR inhibitor resistance, Clin. Cancer Res., 15(10):3484-94 (2009).

Nenna et al., Letter regarding "Immediate effect on fertility of a gluten-free diet in women with untreated coeliac disease", Gut, 60(7):1023-4 (2011).
Nicolin et al., Expression of E-Cadherin During Osteoclast Formation—A Morphological Study, J. Histotechnol., 31(2):51-5 (2008).
Nurwidya et al., Epithelial mesenchymal transition in drug resistance and metastasis of lung cancer, Cancer Res. Treat., 44(3):151-6 (2012).
Okabe et al., Differential constitutive activation of the epidermal growth factor receptor in non-small cell lung cancer cells bearing EGFR gene mutation and amplification, Cancer Res., 67:2046-53 (2007).
Onitsuka et al., Acquired resistance to gefitinib: the contribution of mechanisms other than the T790M, MET, and HGF status, Lung Cancer, 68:198-203 (2010).
Paez-Ribes et al., Antiangiogenic therapy elicits malignant progression of tumors to increased local invasion and distant metastasis, Cancer Cell, 15:220-31 (2009).
Palacios et al., Lysosomal Targeting of E-Cadherin—a Unique Mechanism for the Down-Regulation of Cell-Cell Adhesion during Epithelial to Mesenchymal Transitions, Mol. Cell Biol., 25(1):389-402 (2005).
Pornillos et al., HIV Gag mimics the Tsg101-recruiting activity of the human Hrs protein, J. Chem. Biol., 162(3):425-34 (2003).
Puri et al., Synergism of EGFR and c-Met pathways, cross-talk and inhibition, in non-small cell lung cancer, J. Carcinogenesis, 7:9 (2008).
Qian et al., E-cadherin-mediated adhesion inhibits ligand-dependent activation of diverse receptor tyrosine kinases, The EMBO J., 23:1739-48 (2004).
Raiborg et al., Differential functions of Hrs and ESCRT proteins in endocytic membrane trafficking, Exp. Cell Res., 314:801-13 (2008).
Rao et al., Low-expression of E-cadherin in leukaemia cells causes loss of homophilic adhesion and promotes cell growth, Cell Biol. Int., 35(9):945-51 (2011).
Reagan-Shaw et al., Dose translation from animal to human studies revisited, The FASEB J., 22:659-61 (2007).
Regales et al., Dual targeting of EGFR can overcome a major drug resistance mutation in mouse models of EGFR mutant lung cancer, J. Clin. Invest., 119:3000-10 (2009).
Rho et al., p53 Enhances Gefitinib-Induced Growth Inhibition and Apoptosis by Regulation of Fas in Non-Small Cell Lung Cancer, Cancer Res., 67:1163-9 (2007).
Riches et al., Blood volume determination in the mouse, J. Physiol., 228:279-84 (1973).
Rodriguez et al., E-cadherin's dark side: possible role in tumor progression, Biochim. Biophys. Acta, 1826:23-31 (2012).
Rosell et al., Screening for Epidermal Growth Factor Receptor Mutations in Lung Cancer, N. Engl. J. Med., 361:958-67 (2009).
Sander et al., Rapid disruption of intestinal barrier function by gliadin involves altered expression of apical junctional proteins, FEBS Lett., 579:4851-5 (2005).
Shrader et al., Molecular correlates of gefitinib responsiveness in human bladder cancer cells, Mol. Cancer Ther., 6:277-85 (2007).
Stammati Pagnuzzi et al., Cytotoxic effects of wheat gliadin-derived peptides, Toxicology, 37(3-4):225-32 (1985).
Stockinger et al., E-cadherin regulates cell growth by modulating proliferation-dependent beta-catenin transcriptional activity, J. Cell Biol., 154(6):1185-96 (2001).
Suda et al., Epithelial to mesenchymal transition in an epidermal growth factor receptor-mutant lung cancer cell line with acquired resistance to erlotinib, J. Thorac. Oncol., 6(7):1152-61 (2011).
Taglialatela, CDK12 is a novel oncogene with clinical and pathogenetic relevance in breast cancer, PhD Thesis, European School of Molecular Medicine, University of Milan and University of Naples "Federico II" (2011-2012 academic year).
The Cancer Genome Atlas Research Network, Integrated genomic analyses of ovarian carcinoma, Nature, 474:609-5 (plus erratum) (2011).
Thomson et al., Epithelial to Mesenchymal Transition Is a Determinant of Sensitivity of Non-Small-Cell Lung Carcinoma Cell Lines and Xenografts to Epidermal Growth Factor Receptor Inhibition, Cancer Res., 65:9455-62 (2005).

(56) References Cited

OTHER PUBLICATIONS

Thomson et al., Kinase switching in mesenchymal-like non-small cell lung cancer lines contributes to EGFR inhibitor resistance through pathway redundancy, Clin. Exp. Metastasis, 25(8):843-54 (2008).

Toyoshima et al., Inhibition of Tumor Growth and Metastasis by Depletion of Vesicular Sorting Protein Hrs—Its Regulatory Role on E-Cadherin and b-Catenin, Cancer Res., 67:5162-71 (2007).

Tracy et al., Gefitinib Induces Apoptosis in the EGFRL858R Non-Small-Cell Lung Cancer Cell Line H3255, Cancer Res., 64:7241-4 (2004).

Tu et al., Endosomal-sorting complexes required for transport (ESCRT) pathway-dependent endosomal traffic regulates the localization of active Src at focal adhesions, Proc. Natl. Acad. Sci. USA, 107(37):16107-12 (2010).

Tursi et al., Effect of gluten-free diet on pregnancy outcome in celiac disease patients with recurrent miscarriages, Dig. Dis. Sci., 53:2925-8 (2008).

Vilasi et al., Interaction of toxic and immunogenic A-gliadin peptides with a membrane-mimetic environment, J. Mol. Recognit, 23:322-8 (2010).

Wagner et al., Tsg101 Is Essential for Cell Growth, Proliferation, and Cell Survival of Embryonic and Adult Tissues, Mol. Cell Biol., 23(1):150 (2003).

Warrington et al., Effects of rabeprazole, 20 mg, or esomeprazole, 20 mg on 24-h intragastric pH and serum gastrin in healthy subjects, Aliment. Pharmacol. Ther., 16:1301-7 (2002).

Wedge et al., ZD6474 inhibits vascular endothelial growth factor signaling, angiogenesis, and tumor growth following oral administration, Cancer Res., 62:4645-55 (2002).

Wells et al., E-cadherin as an indicator of mesenchymal to epithelial reverting transitions during the metastatic seeding of disseminated carcinomas, Clin. Exp. Metastasis, 25(6):621-8 (2008).

Witta et al., Restoring E-cadherin expression increases sensitivity to epidermal growth factor receptor inhibitors in lung cancer cell lines, Cancer Res., 66(2):944-50 (2006).

Yao et al., Mechanism of the Mesenchymal-Epithelial Transition and Its Relationship with Metastatic Tumor Formation, Mol. Cancer Res., 9:1608-20 (2011).

Yauch et al., Epithelial versus mesenchymal phenotype determines in vitro sensitivity and predicts clinical activity of erlotinib in lung cancer patients, Clin. Cancer Res., 11(24 Pt. 1):8686-98 (2005).

Yilmaz et al., Mechanisms of motility in metastasizing cells, Mol. Cancer Res., 8(5):629-42 (2010).

Zang et al., Genetic and structural variation in the gastric cancer kinome revealed through targeted deep sequencing, Cancer Res., 71-29-39 (2011).

Zhou et al., Gefitinib Inhibits the Proliferation of Pancreatic Cancer Cells via Cell Cycle Arrest, The Anatomical Record, 292:1122-7 (2009).

Zugna et al., A nationwide population-based study to determine whether coeliac disease is associated with infertility, Gut, 59:1471-5 (2010).

International Preliminary Report on Patentability, corresponding international application No. PCT/US2014/021660, Jun. 11, 2015.

* cited by examiner

KITS AND METHODS FOR THE TREATMENT OF CANCER USING GLIADIN PEPTIDES

CROSS-REFERENCE TO RELATED APPLICATION

This application claims the benefit of priority under 35 U.S.C. §119(e) of U.S. Provisional Patent Application Ser. No. 61/774,285 filed Mar. 7, 2013, which is incorporated herein by reference.

This application contains, as a separate part of the disclosure, a sequence listing in computer-readable form (Filename: 47321A_SeqListing.txt; Size: 795 bytes; Created: Mar. 4, 2014) which is incorporated by reference in its entirety.

FIELD OF THE INVENTION

The invention is directed to kits for treating cancer comprising a gliadin peptide and methods for treating cancer comprising administration of a gliadin peptide to a patient. The gliadin peptide may be co-administered with at least one chemotherapeutic agent such as a receptor tyrosine kinase inhibitor to increase the anticancer effect of the chemotherapeutic agent(s).

BACKGROUND OF THE INVENTION

With millions of people world-wide dying from cancer each year, there is an ever present need for improved therapeutic options. A host of chemotherapeutic agents have been developed in an effort to combat the various forms of the disease. Examples of classes of chemotherapeutic agents include alkylating agents, antibiotics, antimetabolites, differentiating agents, mitotic inhibitors, steroids, topoisomerase inhibitors, and tyrosine kinase inhibitors (TKIs). TKIs block the phosphorylation of proteins to inhibit activation of signal transduction pathways that support tumor development and progression. Receptor tyrosine kinase inhibitors (RTKIs) are TKIs that specifically target the activity of receptor tyrosine kinase (RTK) proteins such as epidermal growth factor receptor (EGFR), fibroblast growth factor receptor (FGFR), platelet-derived growth factor receptor (PDGFR), and vascular endothelial growth factor receptor (VEGFR). However, the effectiveness of RTKIs and other chemotherapy drugs is often hindered by the intrinsic or acquired resistance of cancer cells to anticancer agents.

One contributing factor to the resistance of tumors to chemotherapy is the presence of cancer stem cells (CSCs) within cancer cell populations. CSCs are undifferentiated cells that constitute a small subset (typically less than 10%) of cancer cells. CSCs are so named because they possess some of the characteristics of embryonic stem cells and can differentiate into a variety of cancer cell types. CSCs are therefore tumorigenic and can lead to cancer relapse and metastasis. Many chemotherapeutic drugs kill differentiated cancer cells, but fail to effectively eliminate CSCs, allowing those cells to proliferate and the cancer to persist, resulting in the overall resistance of the tumor to eradication.

Two RTKIs approved for use in treating cancer are erlotinib (Tarceva®, OSI Pharmaceuticals) and gefitinib (Iressa®, AstraZeneca). Both drugs target and inhibit EGFR. Activation of EGFR following the binding of epidermal growth factor (EGF) or another ligand to the receptor results in the ATP-driven phosphorylation of tyrosine residues located in the intracellular domain of the receptor. The phosphorylated tyrosines then interact with other intracellular proteins and activate signal transduction pathways to promote cell survival and proliferation. Increased activation of EGFR is associated with a variety of cancer types, especially tumors derived from epithelial cells. The increase in receptor activity can result from mutations in the kinase domain of EGFR, amplification of EGFR gene expression, or overexpression of the EGFR protein (Yauch et al., *Clinical Cancer Research.* 2005; 11(24):8686-98). Erlotinib and gefitinib, as well as other RTKIs, interfere with the ATP-binding domain of RTKs to suppress receptor activation and block downstream signal transduction.

Erlotinib and gefitinib were the first RTKIs approved for use in treating non-small cell lung cancer (NSCLC). Lung cancer is the leading cause of cancer deaths worldwide, and about 85-90% of lung cancer patients have NSCLC (Gottschling et al. *Lung Cancer.* 2012; 77(1):183-91). The effectiveness of erlotinib and gefitinib in treating NSCLC has been limited, with most patients continuing to exhibit disease progression following initiation of therapy (Witta et al., *Cancer Research.* 2006; 66(2):944-950). Patients with certain EGFR mutations have been found to respond better to treatment with RTKIs than those with wild-type EGFR. Approximately 70-80% of NSCLC patients with EGFR mutations are sensitive to RTKI therapy, however, virtually all patients eventually acquire resistance (Suda et al. *Journal of Thoracic Oncology.* 2011; 6(7):1152-61). Additionally, the prevalence of the mutations is relatively rare, occurring in less than 20% of patients (Yauch 2005, supra). Overall, only about 10% of Caucasian NSCLC patients exhibit significant changes in disease progression following therapy with erlotinib or gefitinib (Gottschling 2012, supra), underscoring the need for improved therapeutic methods.

Gliadin is a protein found in wheat and related grains and is one of the main components of gluten. The four main types of gliadin are alpha, beta, gamma, and omega. Gliadin can be digested into a number of active peptides, including some that trigger T-cell immunity or cytotoxicity. Gliadin has been extensively studied for its role in celiac disease, a chronic inflammatory condition related to dietary gluten, but has not been disclosed or suggested for use as an anticancer agent, either alone or in combination with conventional chemotherapeutic agents. In fact, treatment of various cell types, including cancer cells, with gliadin peptides has been demonstrated to activate the EGFR pathway and induce cell proliferation (Barone et al. *Gut.* 2007; 56(4):480-488), which strongly suggests that gliadin administration is contraindicated for the treatment of cancer.

SUMMARY OF THE INVENTION

The invention provides a kit comprising a pharmaceutical composition comprising a gliadin peptide and instructions for administration of a therapeutically effective amount of the peptide to a patient with cancer. A kit according to the invention may further comprise a pharmaceutical composition comprising at least one chemotherapeutic agent and instructions for co-administering therapeutically effective amounts of the gliadin peptide and chemotherapeutic agent(s) to a patient with cancer.

The invention also provides a method of treating cancer comprising administering a therapeutically effective amount of a gliadin peptide to a patient with cancer. A method according to the invention may further comprise co-administering a therapeutically effective amount of at least one chemotherapeutic agent to a patient with cancer.

The gliadin peptide according to the invention may be an alpha-gliadin peptide. Examples of suitable alpha-gliadin peptides include at least alpha-gliadin peptide p31-43, e.g., alpha-gliadin peptide p31-43, alpha-gliadin peptide p31-49 and alpha-gliadin peptide p31-55. In one aspect, at least one chemotherapeutic agent according to the invention is a RTKI. A RTKI according the invention may be an EGFR inhibitor. Examples of suitable EGFR inhibitors include gefitinib and erlotinib. In one embodiment, co-administration of a gliadin peptide and RTKI to a patient with cancer is effective to decrease or prevent resistance of the cancer to the RTKI.

DETAILED DESCRIPTION OF THE INVENTION

The invention provides kits and methods for treating cancer comprising administering a gliadin peptide to a patient. A kit according to the invention comprises a pharmaceutical composition comprising a gliadin peptide and may further comprise instructions for administration of a therapeutically effective amount of the peptide to a patient with cancer. The kit may further comprise a pharmaceutical composition comprising at least one chemotherapeutic agent such as a RTKI and instructions for co-administering therapeutically effective amounts of the gliadin peptide and chemotherapeutic agent(s) to a patient with cancer. A method of treating cancer according to the invention comprises administering a therapeutically effective amount of a gliadin peptide to a patient with cancer. The method may further comprise co-administering a therapeutically effective amount of at least one chemotherapeutic agent such as a RTKI to a patient with cancer.

The gliadin peptide may be an alpha, beta, gamma, or omega gliadin peptide. In one aspect, the gliadin peptide according to the invention is an alpha-gliadin peptide or a derivative or fragment thereof. Examples of suitable alpha-gliadin peptides include at least alpha-gliadin peptide p31-43, e.g., alpha-gliadin peptide p31-55, alpha-gliadin peptide p31-49, and alpha-gliadin peptide p31-43. In a preferred embodiment, the alpha-gliadin peptide is alpha-gliadin peptide p31-43 or a derivative or fragment thereof. Alpha-gliadin peptide p31-43 has the amino acid sequence LGQQQPFPPQQPY (SEQ ID NO:1) and is often referred to as the "toxic" gliadin peptide because it induces an innate inflammatory immune response and results in intestinal damage. Treatment of cancer cells with alpha-gliadin peptide p31-43 induces cell proliferation (Barone et al. *PLoS ONE*. 2010; 5(8):e12246), so the peptide has not been reported for use in treating tumors, much less included in pharmaceutical compositions or kits for treating tumors. A gliadin peptide according to the invention may be obtained following enzymatic digestion of a gliadin protein or can be chemically synthesized using conventional methods known in the art. A pharmaceutical composition comprising a gliadin peptide comprises the peptide in combination with a pharmaceutically acceptable carrier, diluent, and/or excipient(s). Routes of administration suitable for administering a pharmaceutical composition comprising gliadin to a patient include, but are not limited to, oral, intramuscular, intravenous, respiratory/inhalation, and subcutaneous.

According to the invention, a gliadin peptide can be co-administered with at least one chemotherapeutic agent to a patient with cancer. Examples of chemotherapeutic agents that may be co-administered with a gliadin peptide include, but are not limited to, alkylating agents, antibiotics, antimetabolites, differentiating agents, mitotic inhibitors, steroids, topoisomerase inhibitors, TKIs (such as RTKIs), and combinations thereof. In one aspect, a gliadin peptide can be co-administered with at least one RTKI. Examples of RTKIs include, but are not limited to, afatinib, axitinib, canertinib, cediranib, erlotinib, gefitinib, grandinin, imatinib, lapatinib, leflunomide, lestaurtinib, neratinib, pazopanib, quizartinib, regorafenib, semaxanib, sorafenib, sunitib, sutent, tivozanib, tocerabib, vandetanib, vatalanib, monoclonal antibodies that bind specific RTKs, and combinations thereof. A preferred RTKI according to the invention is an inhibitor of EGFR. Examples of EGFR inhibitors include, but are not limited to, gefitinib and erlotinib. In one embodiment, co-administration of a gliadin peptide and RTKI to a patient with cancer is effective to decrease or prevent resistance of the cancer to the RTKI.

The kits and methods disclosed herein can be used to treat a human patient with cancer or any other mammal. The invention is useful for treating many types of cancer including bladder cancer, breast cancer, colon cancer, endometrial cancer, kidney cancer, leukemia, lung cancer, lymphoma, pancreatic cancer, prostate cancer, skin cancer, and thyroid cancer. The invention is particularly effective for treating cancers whose progression is dependent on changes in intercellular adhesion. In one aspect, the invention is used to treat lung cancer, including NSCLC.

As used herein, the following definitions may be useful in aiding the skilled practitioner in understanding the invention:

The term "therapeutically effective" depends on a patient's condition and the specific compound administered. The term refers to an amount effective to achieve a desired clinical effect. In some embodiments, a therapeutically effective amount is an amount effective to inhibit growth of cancer cells, prevent metastasis, or result in cell death. Therapeutically effective amounts of known chemotherapeutic agents are known in the art. For example, a therapeutically effective amount of a RTKI is generally about 5 mg/kg/day to about 150 mg/kg/day, about 10 mg/kg/day to about 100 mg/kg/day, and/or about 25 mg/kg/day to about 75 mg/kg/day, depending on the drug. For a gliadin peptide, a therapeutically effective amount is generally a dosage necessary to achieve a plasma concentration of about 5 µg/mL to about 200 µg/mL, about 10 µg/mL to about 100 µg/mL, and/or about 15 µg/mL to about 50 µg/mL, for example, about 20 µg/mL. Dosages and the frequency of administration for use according to the present disclosure may vary according to such factors as the route of administration, the nature and severity of the disease to be treated, and the size and general condition of the patient. Appropriate dosages can be determined by procedures known in the pertinent art, e.g., clinical trials that may involve dose escalation studies and protocols described herein. Generally, a clinician titers the dosage and modifies the route of administration to obtain the optimal therapeutic effect. Purely by way of illustration, the dosage of a gliadin peptide needed to achieve a therapeutically effective amount ranges from about 100 µg/kg/day to about 100 mg/kg/day, about 200 µg/kg/day to about 75 mg/kg/day, about 500 µg/kg/day to about 50 mg/kg/day, about 750 µg/kg/day to about 25 mg/kg/day, and/or about 1 mg/kg/day to about 15 mg/kg/day, depending on the factors mentioned above. Some conditions require prolonged treatment, which may or may not entail administering lower doses over multiple administrations. If desired, a dose is administered as two, three, four, five, six or more sub-doses administered separately at appropriate intervals throughout the day. The treatment period will depend on the particular condition and may last one day to several days, weeks, months, or years.

The term "monotherapy" means that a gliadin peptide is administered in a manner such that its pharmacological effects on cancer cells and tumors do not overlap with the pharmacological effects of a chemotherapeutic agent. During monotherapy, a gliadin peptide is necessarily administered alone. Gliadin peptide monotherapy may occur before, after, or both before and after, treatment using a chemotherapeutic agent, so long as the chemotherapeutic agent is no longer therapeutically effective at the time the gliadin peptide is administered.

The terms "co-administering" and "combination therapy" mean that a gliadin peptide and at least one chemotherapeutic agent are administered in a manner that permits all the compounds to exert pharmacological effects during an overlapping period of time. The gliadin peptide and chemotherapeutic agent(s) may be administered in the same pharmaceutical composition or in separate compositions, and via the same or different routes of administration. The gliadin peptide and chemotherapeutic agent(s) may be co-administered at the same time or at different times as long as both compounds exert pharmacological effects during an overlapping period of time. For example, the compounds may both be administered to a patient within a time period of about 2, 4, 6, 8, 12, 24, or 48 hours. Either the gliadin peptide or the chemotherapeutic agent(s) may be administered first. As long as subsequent compounds are administered while a therapeutically effective concentration of the first compound is present, the gliadin peptide and the chemotherapeutic agent(s) are considered to be co-administered in accordance with the teachings of the invention.

The term "chemotherapeutic agent" means any compound that is toxic with respect to cancer cells. A chemotherapeutic agent can be a small molecule, protein, polypeptide, peptide, nucleic acid, and combinations thereof. Exemplary classes of chemotherapeutic agents are provided above. Specific examples of chemotherapeutic agents include, but are not limited to, azacitidine, axathioprine, bevacizumab, bleomycin, capecitabine, carboplatin, chlorabucil, cisplatin, cyclophosphamide, cytarabine, daunorubicin, docetaxel, doxifluridine, doxorubicin, epirubicin, etoposide, fluorouracil, gemcitabine, trastuzumab, idarubicin, mechlorethamine, melphalan, mercaptopurine, methotrexate, mitoxantrone, oxaliplatin, paclitaxel, tafluposide, teniposide, tioguanine, retinoic acid, valrubicin, vinblastine, vincristine, vindesine, vinorelbine, the specific exemplary RTKIs listed above, and combinations thereof. Additional examples of chemotherapeutic agents are known in the art.

The term "receptor tyrosine kinase inhibitor" or "RTKI" means any compound capable of inhibiting the activity of a member of the receptor tyrosine kinase (RTK) family of proteins. A RTKI can be a small molecule, protein, polypeptide, peptide, nucleic acid, and combinations thereof. Examples of protein targets for RTKIs include, but are not limited to, members of the following RTK families: ephrin receptor, epidermal growth factor receptor, fibroblast growth factor receptor, insulin receptor, insulin-like growth factor receptor, neutrophin receptors, platelet-derived growth factor receptor, and vascular endothelial growth factor receptor. Specific exemplary RTKIs are listed above.

The term "derivative or fragment" means a peptide having a structure and biological activity similar to a gliadin peptide. A derivative or fragment shares at least 70%, 80%, or 90% amino acid sequence homology with a gliadin peptide. In various embodiments, a derivative or fragment shares at least 70%, 80%, or 90% amino acid sequence homology with alpha-gliadin peptide p31-55, alpha-gliadin peptide p31-49, or alpha-gliadin peptide p31-43. A derivative or fragment may be a chemically modified gliadin peptide. For example, a derivative or fragment can be a gliadin peptide chemically modified to improve the stability, membrane penetration, or immunogenicity of the peptide. Examples of chemical modifications that can be used to form derivatives and fragments of gliadin peptides include, but are not limited to, polymer conjugation, lipidization, use of amino acid analogs, glycosylation, and cationization. In one aspect, a suitable derivative or fragment of a gliadin peptide contains at least the amino acid sequence PPQQPY (SEQ ID NO:2).

Advantageously, co-administering a gliadin peptide and at least one chemotherapeutic agent such as a RTKI to a patient with cancer is effective to decrease or prevent resistance of the cancer cells to the chemotherapeutic agent(s). The co-administration of a gliadin peptide and at least one chemotherapeutic agent, therefore, increases and prolongs the efficacy of the chemotherapeutic agent(s). While not intending to be bound by a single theory, it is believed that the anticancer effect achieved from administering a gliadin peptide alone or in combination with at least one chemotherapeutic agent according to the invention can be attributed to the impact of the gliadin peptide on the intracellular transport of cargo.

Proteins and other molecules are trafficked within the cytosolic compartment of cells in vesicles known as endosomes as part of the endocytic pathway. Early endosomes are vesicles that receive molecules internalized from the plasma membrane. Early endosomes mature into late endosomes, also known as multivesicular bodies (MVBs). The late endosomes/MVBs eventually fuse with lysosomes, resulting in the enzymatic degradation of the internalized cargo. As an alternative to lysosomal degradation, some molecules are sorted into recycling endosomes and trafficked back to the plasma membrane or to other intracellular sites. Gliadin peptides, particularly alpha-gliadin peptide p31-43, have been shown to interfere with the endocytic pathway by delaying maturation of early endosomes to late endosomes (Barone 2010, supra). Thus, gliadin peptides interfere with the degradation of proteins, chemotherapeutic agents, and other molecules trafficked within endosomes in the cytosolic compartment. By preventing the degradation of intracellular molecules, gliadin peptides can enhance the anticancer activity of chemotherapeutic agents.

The endosomal sorting complex required for transport (ESCRT) protein complexes (ESCRT-0, ESCRT-1, ESCRT-2, and ESCRT-3) regulate the sorting of cargo into MVBs for eventual degradation within lysosomes. Hepatocyte growth factor-regulated tyrosine kinase substrate (HRS), a component of ESCRT-0, regulates the trafficking of molecules in early and late endosomes (Henne et al. *Developmental Cell.* 2011; 21(1):77-91; Barone 2010, supra). Amino acids 719-731 of HRS, located at the carboxyl terminus, contain the binding domains necessary for the localization of HRS to endosomal membranes (Barone 2010, supra). The sequence of HRS amino acids 719-731 (PSQDASLPPQQPY; SEQ ID NO:3) is very similar to the alpha-gliadin peptide p31-43 peptide. Out of 13 residues, seven are identical, including six contiguous amino acids (PPQQPY; SEQ ID NO:2), and two are similar between the sequences, with the only significant difference being an N-terminal leucine in alpha-gliadin peptide p31-43 compared to the proline in HRS 719-731 (Barone 2010, supra). Alpha-gliadin peptides comprising at least alpha-gliadin p31-43, e.g., alpha-gliadin peptide p31-43, alpha-gliadin peptide p31-49 and alpha-gliadin peptide p31-55, can therefore compete with HRS binding, thereby interfering with HRS localization within endosomal membranes (Barone 2010, supra). As a result, after cells are treated with alpha-gliadin peptide p31-43, the amount of HRS in the cytosol is increased while membrane-associated HRS is decreased (Barone 2010, supra). The decreased presence of HRS in the endosomal membranes disrupts the normal trafficking of cargo within the cell, leading to impaired degradation of intracellular molecules. By promoting the retention of cargo, including toxic molecules, that would otherwise ordinarily be removed from the cell, administration of gliadin peptides to a patient is able to decrease cell viability, which supports the use of the peptides for the treatment of cancer.

In addition to their potential for use in treating cancer without additional therapeutic agents, gliadin peptides also show promise for use in combination with one or more chemotherapeutic agents because the impact of the peptides on the endocytic pathway can affect the trafficking of chemotherapeutic agents and their targets. After out-competing HRS for binding sites associated with endosomal membranes, alpha-gliadin peptides comprising at least alpha-gliadin p31-43, e.g., alpha-gliadin peptide p31-43, alpha-gliadin peptide p31-49 and alpha-gliadin peptide p31-55, localize to endosomes. Vesicles carrying alpha-gliadin peptides comprising at least alpha-gliadin peptide p31-43 move more slowly than normal vesicles (Barone 2010, supra). The delay of intracellular transport induced by alpha-gliadin peptide p31-43 is not influenced by the cargo within the vesicles, so all molecules trafficked intracellularly, including chemotherapeutic agents, are potentially affected (Barone 2010, supra). The prolonged cytosolic transit of cargo can extend the time in which a chemotherapeutic agent is able to accumulate, leading to higher intracellular concentrations of drug and increased cytotoxicity. The extended presence of the drug within the cell also allows the drug to exert its pharmacological effect within a cell for a longer period of time, enhancing the drug's efficacy. Co-administration of a gliadin peptide with at least one chemotherapeutic agent can therefore potentiate the activity of a wide range of anticancer drugs having various mechanisms of action.

The effect of gliadin peptides on the endocytic pathway can also exert anticancer therapeutic effects by influencing cellular phenotype. Epithelial and mesenchymal are two main classes of cellular phenotypes. Epithelial cells are highly organized, with numerous cell junctions maintaining adherence between neighboring cells. In contrast, mesenchymal cells are disorganized and lack strong intercellular junctions, which increases their migratory potential. During a process known as the mesenchymal transition (MT), epithelial cells and non-epithelial cells differentiate into mesenchymal cells. The transition results in the loss of cell-cell adhesion and increased cell motility, as well as increased resistance to apoptosis, thereby promoting the invasiveness, i.e., metastasis, of tumors. During MT, expression of cell junction proteins such as e-cadherin is decreased, and expression of mesenchymal markers such as vimentin and fibronectin increases.

Low expression of e-cadherin has been associated with the progression of a number of cancer types (Rao et al. *Cell Biol. Int.* 2011; 35(9):945-51; Yilmaz et al. *Molecular Cancer Research*. 2010; 1; 8(5):629-42). Administration of a gliadin peptide can prevent a mesenchymal phenotype by impairing e-cadherin degradation and promoting recycling of the junction protein back to the plasma membrane to maintain cell-to-cell adhesion. The effect of gliadin on e-cadherin retention may explain why the presence of plasma gliadin leads to reduced enterocyte height and villous atrophy in untreated celiac patients (Barone 2010, supra) because changes in cellular adhesion through the loss of e-cadherin are necessary to promote vertical growth of intestinal cells. Additionally, by interfering with HRS and the ESCRT complexes, gliadin peptides can prevent the degradation of focal adhesions that connect cells to the extracellular matrix (Tu et al. *Proceedings of the National Academy of Sciences*. 2010; 107(37):16107-12). The intact focal adhesions also help maintain the non-mesenchymal phenotype and inhibit transition to a mesenchymal state. Because administration of a gliadin peptide according to the invention can block MT and prevent cell growth and cellular migration (and thus metastasis of cancer cells), the treatment according to the invention can effectively control a spectrum of cancer types.

The effect of gliadin peptides on MT can also increase the efficacy of co-administered chemotherapeutic agents. Tumor metastasis complicates cancer treatment and is a major contributor to patient death. A mesenchymal phenotype has been identified as predictive of drug sensitivity, with expression of mesenchymal markers signaling a poor response to chemotherapy (Yauch 2005, supra; Buck et al. *Molecular Cancer Therapeutics*. 2007; 6(2):532-41; Frederick et al. *Molecular Cancer Therapeutics*. 2007; 6(6):1683-1691). E-cadherin expression is substantially absent in resistant cancer cell lines, and restoration of e-cadherin expression can increase drug sensitivity, resulting in cell growth inhibition and apoptosis following treatment (Witta 2006, supra). The administration of gliadin peptides to promote retention of e-cadherin and a non-mesenchymal phenotype can therefore improve the response of cancer cells to a co-administered chemotherapeutic agent. For example, a mesenchymal phenotype is associated with lower amounts of e-cadherin and with both intrinsic and acquired resistance to EGFR-specific RTKIs in NSCLC (Suda 2011, supra). Non-mesenchymal cells rely on EGFR-mediated pathways for cell survival and proliferation, but in the mesenchymal state, EGFR signaling is reduced and cells are believed to rely on EGFR-independent mechanisms for cell survival and proliferation (Thomson et al. *Clin. Exp. Metastasis*. 2008; 25(8):843-54). Use of a gliadin peptide to maintain e-cadherin and prevent transition to a mesenchymal state will therefore decrease drug resistance and prolong the sensitivity of cancer calls to the cytotoxic effects of an EGFR-specific RTKI such as gefitinib or erlotinib. Co-administration of a gliadin peptide is expected to act synergistically with other classes of chemotherapeutic agents as well, resulting in improved options for combination therapy to treat cancer.

The anticancer effect achieved from administering a gliadin peptide alone or in combination with at least one chemotherapeutic agent according to the invention may also be attributed to the unexpected advantageous effect of the gliadin peptide on undifferentiated cells. Gliadin peptides are surprisingly effective at killing CSCs that are resistant to other chemotherapeutic agents, rendering them an effective anticancer agent when used alone, i.e., as monotherapy. For example, a gliadin peptide may be administered as an initial (first-line) therapy, i.e., before other anticancer therapies (e.g., chemotherapeutic agents, radiation, and/or surgery) are attempted. As another example, a gliadin peptide may be administered as a subsequent (e.g., second- or third-line) therapy following an anticancer therapy that is no longer therapeutically effective.

The therapeutic effect of a gliadin peptide administered alone as a monotherapy compared to gliadin co-administered with a chemotherapeutic agent may be affected by the mechanism of action of the chemotherapeutic agent. In particular, monotherapy administration of a gliadin peptide following treatment with a chemotherapeutic agent whose main site of action is in the nucleus, e.g., alkylating agents, antibiotics, topoisomerase inhibitors, and other agents that damage DNA, has been found to be surprisingly effective at inhibiting resistant cancer cells that survive treatment with the chemotherapeutic agent, particularly relative to co-administration of both compounds. For such chemotherapeutic agents, it is theorized that monotherapy using a gliadin peptide may prevent interference with the localization of the chemotherapeutic agent to the nucleus (whereas it is theorized that co-administration can promote such interference, thereby possibly attenuating the therapeutic effect of the chemotherapeutic agent). For chemotherapeutic agents whose primary site of action is outside the nucleus, e.g., differentiating agents, mitotic inhibitors, steroids, and TKIs, co-administration of a gliadin peptide and the chemotherapeutic agent is surprisingly effective at inhibiting cancer cell growth and can surprisingly achieve synergistic therapeutic efficacy greater than monotherapy with the gliadin peptide or chemotherapeutic agent alone. The administration of a gliadin peptide before and/or after treatment with at least one chemotherapeutic (e.g., monotherapy when the compounds do not exert pharmacological effects during an overlapping period of time) or during administration of at least one chemotherapeutic (i.e, co-administration when the compounds do exert pharmacological effects during an overlapping period of time) is therefore effective to decrease the number of CSCs and prevent cancer relapse and metastasis.

The ability of gliadin peptides to increase the therapeutic efficacy of a co-administered chemotherapeutic agent may also be attributable in part to the interaction of the gliadin peptide with proteins important for maintaining an undifferentiated phenotype. In addition to HRS, the alpha gliadin peptide p31-43 shares the six amino acid sequence PPQQPY (SEQ ID NO: 2) with residues found within the kinase domain of cyclin-dependent kinase 12 (CDK12). The kinase domain of CDK12 is important for its interaction with cyclin K (CycK) (Dai et al., *J. Biol. Chem.* 2012; 287(30):25344-52). Both CDK12 and CycK are highly expressed in embryonic stem cells, but their expression decreases upon differentiation (Dai 2012, supra). The proteins are important for self-renewal of embryonic stem cells, and inhibition of either leads to cell differentiation (Dai 2012, supra). Based on the foregoing and the results shown in the Examples below, it is believed that alpha-gliadin peptide p31-43 may interfere with the interaction between CDK12 and CycK and inhibit the activity of the two proteins, thereby promoting cellular differentiation and potentially increasing the sensitivity of the tumor to the chemotherapeutic agent. The abilities of gliadin peptides to kill CSCs and/or promote cellular differentiation unexpectedly provide advantages not obtained from other chemotherapeutic agents. The therapeutic efficacy achievable using a combination of a gliadin peptide and at least one chemotherapeutic agent to treat cancer is surprising and unexpected considering the characterization of the activity of the compounds as being contrary. For example, gliadin peptides are known to drive cells into S-phase of the cell cycle, thereby promoting cell proliferation (Barone 2007, supra), while chemotherapeutic agents generally are cytotoxic, particularly to rapidly dividing cells. RTKIs such as erlotinib and gefitinib generally act to arrest cells in G1-phase to inhibit cell growth (Arora et al., *JPET.* 2005; 315(3):971-79). Thus, the activity of a gliadin peptide and chemotherapeutic agent would be expected to at least counteract each other. Similarly, the activity of an EGFR activator such as a gliadin peptide and an EGFR inhibitor such as a RTKI would be expected to be contrary to each other. However, because gliadin peptides cause EGFR and other receptors to be recycled back to the cell membrane instead of degraded within lysosomes, the time during which EGFR remains phosphorylated is extended (Barone 2007, supra; Barone 2010, supra). Such a prolonged activation of EGFR and other RTKs may increase the sensitivity of the cells to RTKIs. The co-administration of a gliadin peptide and an EGFR-specific RTKI is therefore effective for treating patients with wild-type EGFR and those expressing mutant receptor proteins.

The co-administration of a gliadin peptide and at least one chemotherapeutic agent such as a RTKI provides an unexpected and surprisingly effective anticancer therapy. The gliadin peptide acts in concert with the chemotherapeutic agent(s) to achieve enhanced therapeutic efficacy. When a gliadin peptide and RTKI are co-administered to a patient with cancer, resistance of the cancer to the RTKI is decreased or prevented. A patient suffering from both untreated celiac disease and cancer could be expected to respond better to anti-cancer therapy using RTKIs or other chemotherapeutic agents. Celiac disease is a chronic inflammatory disease of the small intestine that involves an immunogenic response to wheat gluten and similar proteins. Adopting a gluten-free diet mitigates the symptoms of celiac disease. In patients suffering from celiac disease, gliadin peptides are resistant to degradation and transported intact into serum in significantly higher amounts compared to healthy subjects and patients with treated celiac disease (Matysiak-Budnik et al. *Gastroenterology.* 2003; 125(3):696-707), creating a condition known as "leaky gut syndrome." The increased permeability of gliadin through the lining of the digestive track and into systemic circulation would allow gliadin peptides to reach tumor sites and increase the sensitivity of the cancer cells to chemotherapy. Thus, according to one aspect, the patient to be treated is not suffering from celiac disease.

The invention is further explained by the following Examples which should not be construed as limiting its scope.

Example 1

Cancer cells of various types including NSCLC are obtained from American Type Culture Collection (ATCC; Manassas, Va.) or biopsies from cancer patients and maintained in growth medium. Cells are plated in multi-well cell culture plates and divided into the following experimental groups: (1) cells incubated with growth medium only; (2) cells incubated with growth medium supplemented with multiple concentrations of alpha-gliadin peptide p31-43, alpha-gliadin peptide p31-49, or alpha-gliadin peptide p31-55 from 5 µg/mL to 200 µg/mL; (3) cells incubated with growth medium supplemented with multiple concentrations of erlotinib from 0.1 uM to 10 uM; (4) cells incubated with growth medium supplemented with 5 µg/mL to 200 µg/mL alpha-gliadin peptide p31-43, alpha-gliadin peptide p31-49, or alpha-gliadin peptide p31-55 and 0.1 µM to 10 µM erlotinib; (5) cells incubated with growth medium supplemented with multiple concentrations of gefitinib from 0.1 µM to 10 µM; and (6) cells incubated with growth medium supplemented with 5 µg/mL to 200 µg/mL alpha-gliadin peptide p31-43, alpha-gliadin peptide p31-49, or alpha-gliadin peptide p31-55 and 0.1 µM to 10 µM gefitinib.

Cell viability is measured after 3 to 5 days and the half-maximal inhibitor concentration ($IC_{50}$) is determined from the dose-response curve. Co-treatment with a gliadin peptide and erlotinib significantly decreases the $IC_{50}$ of erlotinib compared to the $IC_{50}$ for erlotinib administered alone. Similarly, co-treatment with a gliadin peptide and gefitinib significantly decreases the $IC_{50}$ of gefitinib compared to the $IC_{50}$ of gefitinib administered alone.

Example 2

Mice are injected subcutaneously with NSCLC cells in the flank region. Tumors are allowed to grow to about 100 cubic millimeters to 200 cubic millimeters. The animals are divided into the following experimental groups and treated for 14 days: (1) animals receiving a once daily saline injection into the tumor site; (2) animals receiving a once daily injection of 5 µg/mL to 200 µg/mL of alpha-gliadin peptide p31-43, alpha-gliadin peptide p31-49, or alpha-gliadin peptide p31-55 into the tumor site; (3) animals receiving a once daily oral dose of up to 100 mg/kg erlotinib; (4) animals receiving a once daily oral dose of up to 100 mg/kg gefitinib; (5) animals receiving a once daily injection of 5 µg/mL to 200 µg/mL of alpha-gliadin peptide p31-43, alpha-gliadin peptide p31-49, or alpha-gliadin peptide p31-55 into the tumor site and once daily oral dose of up to 100 mg/kg erlotinib; (6) animals receiving a once daily injection of 5 µg/mL to 200 µg/mL alpha-gliadin peptide p31-43, alpha-gliadin peptide p31-49, or alpha-gliadin peptide p31-55 into the tumor site and once daily oral dose of up to 100 mg/kg gefitinib.

Tumor volumes are evaluated using calipers over the course of treatment to determine growth inhibition. Co-administration of a gliadin peptide and erlotinib or a gliadin peptide and gefitinib results in a significant inhibition of tumor growth compared to administration of erlotinib or gefitinib alone.

Example 3

An efficacy study in humans is conducted to evaluate the effect of co-administration of (1) alpha-gliadin peptide p31-43, alpha-gliadin peptide p31-49, or alpha-gliadin peptide p31-55 and gefitinib or (2) alpha-gliadin peptide p31-43, alpha-gliadin peptide p31-49, or alpha-gliadin peptide p31-55 and erlotinib in patients with NSCLC. Control group patients are dosed with up to 250 mg daily of gefitinib or up to 150 mg daily of erlotinib. In the experimental group, patients are administered alpha-gliadin peptide p31-43, alpha-gliadin peptide p31-49, or alpha-gliadin peptide p31-55 daily in addition to gefitinib or erlotinib. The alpha-gliadin peptide p31-43, alpha-gliadin peptide p31-49, or alpha-gliadin peptide p31-55 is administered to achieve a plasma concentration of about 5 µg/mL to about 200 µg/mL. Tumor mass and metastasis are evaluated after one, two, and three months of therapy. Patients receiving a gliadin peptide in addition to a RTKI exhibit a significantly reduced primary tumor mass in the lungs compared to patients receiving a RTKI alone. Patients receiving the combination therapy also exhibit significantly fewer metastatic tumors compared to the control group patients. The clinical trial demonstrates the value of including administration of a gliadin peptide in combination therapy to treat cancer.

Example 4

For Examples 4 to 8, human cancer cell lines A549, NC1-H1975, and PANC-1 were obtained from ATCC and maintained in RPMI 1640 media (Life Technologies, Inc., Grand Island, N.Y.) containing 10% fetal bovine serum, 2 mM L-glutamine and 1% antibiotic-antimycotic solution (10 units/µL penicillin, 10 µg/µL streptomycin and 25 µg/mL amphotericin B). Cells were kept at 37° C. in a humidified atmosphere of 5% $CO_2$ and grown until they reached a confluency of 90%. Cells were then washed, trypsinized, and counted using a Coulter counter. (Beckman, Brea, Calif.).

A549 NSCLC cells were maintained and cultured as described above. Alpha-gliadin peptide p31-43 (Anaspec Inc., Fremont, Calif.), gefitinib (LC Laboratories, Woburn, Mass.), and erlotinib (LC Laboratories) were used to treat the cells. Cells were plated at a density of 10,000 cells/well in 24-well cell culture plates and allowed to adhere for 24 hours. The cells were then incubated for 72 hours with the following: (1) vehicle (DMSO/water); (2) 5 µg/mL, 20 µg/mL, or 70 µg/mL alpha-gliadin peptide p31-43; (3) 1 µM gefitinib in DMSO/water; (4) 1 µM erlotinib; (5) 5 µg/mL, 20 µg/mL, or 70 µg/mL alpha-gliadin peptide p31-43 and 1 µM gefitinib in DMSO/water; or (6) 5 µg/mL, 20 µg/mL, or 70 µg/mL alpha-gliadin peptide p31-43 and 1 µM erlotinib in DMSO/water. All experiments were conducted in sextuplicate. For combination therapy using alpha-gliadin peptide p31-43 and gefitinib/erlotinib, the two compounds were administered to the cells simultaneously. Following 72 hours of treatment, growth inhibition was evaluated by the 3-(4,5-dimethylthiazol-2-yl)-2,5-diphenyltetrazolium bromide (MTT) assay (Roche Diagnostics Corporation, Indianapolis, Ind.) according to the manufacturer's instructions. The absorbance at 570 nm was measured using a plate reader (BioTek, Winooski, Vt.). Table 1 shows the mean absorbance at 570 nm and the percent growth inhibition for gliadin- and RTKI-treated A549 cells compared to vehicle-treated cells.

TABLE 1

Effects of alpha-gliadin peptide p31-43 alone or in combination with gefitinib or erlotinib on A549 cell proliferation following 72-hour treatment

| Dose | Mean absorbance (570 nm) | S.E. | % Inhibition | p-value |
|---|---|---|---|---|
| Control (DMSO/water) | 1.49 | 0.35 | — | — |
| 5 µg/mL gliadin | 1.54 | 0.25 | 0 | p > 0.05 |
| 20 µg/mL gliadin | 1.44 | 0.15 | 3.4 | p > 0.05 |
| 70 µg/mL gliadin | 1.35 | 0.18 | 9.4 | p > 0.05 |
| 1 µg/mL gefitinib | 1.35 | 0.19 | 9.4 | p > 0.05 |
| 1 µg/mL erlotinib | 1.44 | 0.12 | 3.4 | p > 0.05 |
| 5 µg/mL gliadin + 1 µg/mL erlotinib | 1.50 | 0.12 | 0 | p > 0.05 |
| 20 µg/mL gliadin + 1 µg/mL erlotinib | 1.19 | 0.08 | 20.1 | p > 0.05 |
| 70 µg/mL gliadin + 1 µg/mL erlotinib | 0.86 | 0.04 | 42.3 | p < 0.05 |
| 5 µg/mL gliadin + 1 µg/mL gefitinib | 1.24 | 0.04 | 16.8 | p > 0.05 |
| 20 µg/mL gliadin + 1 µg/mL gefitinib | 1.14 | 0.02 | 23.5 | p > 0.05 |
| 70 µg/mL gliadin + 1 µg/mL gefitinib | 1.30 | 0.16 | 12.8 | p > 0.05 |

A549 cells treated with alpha-gliadin peptide p31-43 alone at a dose of 20 µg/mL or 70 µg/mL exhibited comparable growth inhibition compared to cells treated with gefitinib or erlotinib alone. Treatment with a combination of alpha-gliadin peptide p31-43 and gefitinib or erlotinib resulted in increased growth inhibition compared to alpha-gliadin peptide p31-43 or each RTKI alone. Co-administration of alpha-gliadin peptide p31-43 and gefitinib or erlotinib surprisingly had a synergistic effect on growth inhibition, with the combination therapy resulting in greater growth inhibition than the sum of the individual growth inhibitory effects of the alpha-gliadin peptide p31-43 and the RTKI.

Overall, the results demonstrated that a gliadin peptide administered alone was an effective anticancer treatment and inhibited cancer cell growth as well as a benchmark chemotherapeutic agent. Combination therapy using a gliadin peptide and a RTKI advantageously resulted in increased inhibition of cancer cell growth compared to either the gliadin peptide or RTKI alone and also produced a surprising and unexpected synergistic antitumor effect.

Example 5

NC1-H1975 NSCLC cells were maintained and cultured as described in Example 4. NC1-H1975 cells harbor an activating mutation in EGFR (L858R) and an additional mutation (T790M), which confers resistance to EGFR TKIs including erlotinib and gefitinib. Alpha-gliadin peptide p31-43, gefitinib, and erlotinib were used to treat the cells. Cells were plated at a density of 10,000 cells/well in 24-well cell culture plates and allowed to adhere for 24 hours. The cells were then incubated for 72 hours with the following: (1) vehicle (DMSO/water); (2) 5 µg/mL, 20 µg/mL, or 70 µg/mL alpha-gliadin peptide p31-43 in DMSO/water; (3) 1 µM gefitinib in DMSO/water; (4) 1 µM erlotinib in DMSO/water; (5) 5 µg/mL, 20 µg/mL, or 70 µg/mL alpha-gliadin peptide p31-43 and 1 µM gefitinib in DMSO/water; or (6) 5 µg/mL, 20 µg/mL, or 70 µg/mL alpha-gliadin peptide p31-43 and 1 µM erlotinib in DMSO/water. All experiments were conducted in sextuplicate. For combination therapy using alpha-gliadin peptide p31-43 and gefitinib/erlotinib, the two compounds were administered to the cells simultaneously. Following 72 hours of treatment, growth inhibition was evaluated by the MTT assay according to the manufacturer's instructions. The absorbance at 570 nm was measured using a plate reader. Table 2 shows the mean absorbance at 570 nm and the percent growth inhibition for gliadin- and RTKI-treated NC1-H1975 cells compared to vehicle-treated cells.

TABLE 2

Effects of alpha-gliadin peptide p31-43 alone or in combination with gefitinib or erlotinib on NCI-H1975 cell proliferation following 72-hour treatment

| Dose | Mean absorbance (570 nm) | S.E. | % Inhibition | p-value |
|---|---|---|---|---|
| Control (DMSO/water) | 2.04 | 0.17 | — | — |
| 5 µg/mL gliadin | 1.51 | 0.08 | 26.0 | p < 0.05 |
| 20 µg/mL gliadin | 1.61 | 0.13 | 21.1 | p > 0.05 |
| 70 µg/mL gliadin | 1.30 | 0.07 | 36.3 | p < 0.001 |
| 1 µg/mL gefitinib | 1.68 | 0.15 | 17.6 | p > 0.05 |
| 1 µg/mL erlotinib | 1.73 | 0.11 | 15.2 | p > 0.05 |
| 5 µg/mL gliadin + 1 µg/mL erlotinib | 1.23 | 0.10 | 39.7 | p < 0.001 |
| 20 µg/mL gliadin + 1 µg/mL erlotinib | 1.00 | 0.11 | 51.0 | p < 0.001 |
| 70 µg/mL gliadin + 1 µg/mL erlotinib | 1.24 | 1.12 | 39.2 | p < 0.001 |
| 5 µg/mL gliadin + 1 µg/mL gefitinib | 1.33 | 0.05 | 34.8 | p < 0.001 |
| 20 µg/mL gliadin + 1 µg/mL gefitinib | 1.11 | 0.06 | 45.6 | p < 0.001 |
| 70 µg/mL gliadin + 1 µg/mL gefitinib | 0.79 | 0.06 | 61.3 | p < 0.001 |

NC1-H1975 cells treated with alpha-gliadin peptide p31-43 alone exhibited significant growth inhibition compared to control cells. The growth inhibition in cells treated with alpha-gliadin peptide p31-43 alone was greater than in cells treated with gefitinib or erlotinib alone. Treatment with a combination of alpha-gliadin peptide p31-43 and gefitinib or erlotinib achieved significant growth inhibition of the cancer cells at all concentrations tested. Additionally, the combination therapy resulted in increased growth inhibition compared to alpha-gliadin peptide p31-43 or each RTKI alone. As shown in Table 2, co-administration of alpha-gliadin peptide p31-43 and gefitinib or erlotinib surprisingly was able to have a synergistic effect on growth inhibition, with the combination therapy resulting in greater growth inhibition than the sum of the individual growth inhibitory effects of the alpha-gliadin peptide p31-43 and the RTKI.

Overall, the results demonstrated that a gliadin peptide administered alone was effective at significantly inhibiting the growth of RTKI-resistant cancer cells and achieved greater therapeutic efficacy than a benchmark RTKI. Combination therapy using a gliadin peptide and a RTKI advantageously resulted in significantly increased inhibition of cancer cell growth compared to either the gliadin peptide or RTKI alone and also produced a surprising and unexpected synergistic antitumor effect.

Example 6

PANC-1 pancreatic carcinoma cells were maintained and cultured as described in Example 4. Alpha-gliadin peptide p31-43, gefitinib, and erlotinib were used to treat the cells. Cells were plated at a density of 10,000 cells/well in 24-well cell culture plates and allowed to adhere for 24 hours. The cells were then incubated for 72 hours with the following: (1) vehicle (DMSO/water); (2) 5 µg/mL, 20 µg/mL, or 70 µg/mL alpha-gliadin peptide p31-43 in DMSO/water; (3) 1 µM gefitinib in DMSO/water; (4) 1 µM erlotinib in DMSO/water; (5) 5 µg/mL, 20 µg/mL in DMSO/water, or 70 µg/mL alpha-gliadin peptide p31-43 and 1 µM gefitinib in DMSO/water; or (6) 5 µg/mL, 20 µg/mL, or 70 µg/mL alpha-gliadin peptide p31-43 and 1 µM erlotinib in DMSO/water. All experiments were conducted in sextuplicate. For combination therapy using alpha-gliadin peptide p31-43 and gefitinib/erlotinib, the two compounds were administered to the cells simultaneously. Following 72 hours of treatment, growth inhibition was evaluated by the MTT assay according to the manufacturer's instructions. The absorbance at 570 nm was measured using a plate reader. Table 3 shows the mean absorbance at 570 nm and the percent growth inhibition for gliadin- and RTKI-treated PANC-1 compared to vehicle-treated cells.

TABLE 3

Effects of alpha-gliadin peptide p31-43 alone or in combination with gefitinib or erlotinib on PANC-1 cell proliferation following 72-hour treatment

| Dose | Mean absorbance (570 nm) | S.E. | % Inhibition | p-value |
|---|---|---|---|---|
| Control (DMSO/water) | 1.87 | 0.11 | — | — |
| 5 µg/mL gliadin | 1.59 | 0.18 | 15.0 | p > 0.05 |
| 20 µg/mL gliadin | 1.39 | 0.15 | 25.7 | p > 0.05 |
| 70 µg/mL gliadin | 1.38 | 0.14 | 26.2 | p > 0.05 |
| 1 µg/mL gefitinib | 2.11 | 0.12 | 0 | p > 0.05 |
| 1 µg/mL erlotinib | 1.98 | 0.20 | 0 | p > 0.05 |
| 5 µg/mL gliadin + 1 µg/mL erlotinib | 1.35 | 0.11 | 27.7 | p > 0.05 |
| 20 µg/mL gliadin + 1 µg/mL erlotinib | 1.75 | 0.07 | 6.4 | p > 0.05 |
| 70 µg/mL gliadin + 1 µg/mL erlotinib | 1.22 | 0.02 | 34.8 | p < 0.05 |
| 5 µg/mL gliadin + 1 µg/mL gefitinib | 1.33 | 0.06 | 28.9 | p > 0.05 |
| 20 µg/mL gliadin + 1 µg/mL gefitinib | 1.15 | 0.05 | 38.5 | p < 0.001 |
| 70 µg/mL gliadin + 1 µg/mL gefitinib | 1.14 | 0.07 | 39.0 | p < 0.001 |

PANC-1 cells treated with alpha-gliadin peptide p31-43 alone exhibited greater growth inhibition than cells treated with gefitinib or erlotinib alone. Treatment with a combination of alpha-gliadin peptide p31-43 and gefitinib or erlotinib achieved significant growth inhibition of the cancer cells. Additionally, the combination therapy resulted in significantly increased growth inhibition compared to alpha-gliadin peptide p31-43 or each RTKI alone. As shown in Table 3, co-administration of alpha-gliadin peptide p31-43 and gefitinib or erlotinib surprisingly could have a synergistic effect on growth inhibition, with the combination therapy resulting in greater growth inhibition than the sum of the individual growth inhibitory effects of the alpha-gliadin peptide p31-43 and the RTKI.

Overall, the results demonstrated that a gliadin peptide administered alone was effective at inhibiting the growth of RTKI-resistant cancer cells and achieved greater therapeutic efficacy than a benchmark RTKI. Combination therapy using a gliadin peptide and a RTKI advantageously resulted in significantly increased inhibition of cancer cell growth compared to either the gliadin peptide or RTKI alone and also produced a surprising and unexpected synergistic antitumor effect. Examples 4 to 6 demonstrated that co-administration of a gliadin peptide and a chemotherapeutic agent provided an advantageous therapeutic effect.

Example 7

PANC-1 human pancreatic carcinoma cells (ATCC) were maintained and cultured as described in Example 4. Alpha-gliadin peptide p31-43 and 5-Fluorouracil (5-FU) (Fisher Scientific, Pittsburgh, Pa.) were used to treat the cells. Cells (passage 27) were plated at a density of $1 \times 10^4$ cells/well in 24-well cell culture plates and allowed to adhere for 24 hours. Cells were then incubated with vehicle (water) or 5-FU at increasing concentrations for 72 hours. All experiments were conducted in triplicate. After incubation with 5-FU at concentrations ranging from 0 μM to 400 μM, cells were detached with trypsin and counted. Table 4 shows the mean cell number and percent growth inhibition following treatment with 5-FU.

TABLE 4

Anti-proliferative effects of 5-FU on PANC-1 cells following 72-hour treatment

| 5-FU Dose (μM) | Mean Cell Number/mL | S.E. | % Inhibition | p-value |
| --- | --- | --- | --- | --- |
| 0 (vehicle) | 317,600 | 7,738 | — | — |
| 6.25 | 116,500 | 2,342 | 63.3 | p < 0.001 |
| 12.5 | 117,500 | 4,474 | 63.0 | p < 0.001 |
| 25.0 | 118,200 | 4,288 | 62.8 | p < 0.001 |
| 50.0 | 100,200 | 1,791 | 63.0 | p < 0.001 |
| 100.0 | 117,600 | 2,006 | 68.5 | p < 0.001 |
| 200.0 | 83,900 | 1,895 | 73.6 | p < 0.001 |
| 400.0 | 66,200 | 1,935 | 79.2 | p < 0.001 |

Cells (passage 30) were then plated at a density of $5 \times 10^3$ cells/well in 24-well cell culture plates and allowed to adhere for 24 hours. Cells were incubated with the following: (1) vehicle (DMSO/water); (2) 6.25 μM 5-FU; (3) 70 μg/mL alpha-gliadin peptide p31-43; (4) 6.25 μM 5-FU and 70 μg/mL alpha-gliadin peptide p31-43 (high combination); or (5) 3.1 μM 5-FU and 35 μg/mL alpha-gliadin peptide p31-43 (low combination). All treatments were conducted in triplicate. For combination therapy using alpha-gliadin peptide p31-43 and 5-FU, the two compounds were administered to the cells simultaneously. Media was refreshed with the respective treatments every 72 hours. After 14 days of treatment, cells were trypsinized and counted. Table 5 shows the mean cell number and percent growth inhibition following treatment.

TABLE 5

Effects of 5-FU alone or in combination with alpha-gliadin peptide p31-43 on PANC-1 cell proliferation following a 14-day treatment regimen

| Dose | Mean Cell Number/mL | S.E. | % Inhibition | p-value |
| --- | --- | --- | --- | --- |
| 0 (vehicle) | 810,467 | 1300 | — | — |
| 6.25 μM 5-FU | 33,233 | 255 | 96 | p < 0.001 |
| 70 μg/mL gliadin | 833,800 | 9500 | 0 | p > 0.05 |
| 6.25 μM 5-FU + 70 μg/mL gliadin | 49,367 | 575 | 94 | p < 0.001 |
| 3.1 μM 5-FU + 35 μg/mL gliadin | 42,033 | 135 | 95 | p < 0.001 |

In order to examine the effects of alpha-gliadin peptide p31-43 on PANC-1 cells exposed to 5-FU for an extended period of time (14 days), an experiment was conducted on the surviving, i.e., resistant, cell population (4%) from the previous experiment. Briefly, after counting viable cells on day 14 of treatment, surviving cells were replated at a density of 5,000 cells per well. The following day, cells were treated with vehicle or 100 μg/mL or 200 μg/mL of alpha-gliadin peptide p31-43. Media containing the respective treatments was refreshed on day 3 and 6. On day 7, cells were trypsinized and counted. Table 6 shows the mean cell number and percent growth inhibition following treatment with alpha-gliadin peptide p31-43.

TABLE 6

Effects of alpha-gliadin peptide p31-43 on surviving cell population of 5-FU-resistant PANC-1 cells

| Dose | Cell Number/mL | % Inhibition |
| --- | --- | --- |
| Control | 8200 | — |
| 100 μg/ml gliadin | 3700 | 55% |
| 200 μg/ml gliadin | 1900 | 77% |

The chemotherapeutic agent 5-FU, which damages DNA, suppressed proliferation of PANC-1 pancreatic cancer cells. The drug inhibited growth of PANC-1 cells by 96% following treatment with 6.25 μM for 14 days. Co-administration of 5-FU and a gliadin peptide achieved significant growth inhibition compared to control cells. The results shown in Tables 3 and 5 suggest that the therapeutic efficacy of co-administering a gliadin peptide and a chemotherapeutic agent compared to either alone could be affected by the site of action (nucleus or cytoplasm) of the chemotherapeutic agent.

Surprisingly, monotherapy administration of a gliadin peptide alone was effective in killing the cancer cells that prior treatment with 5-FU did not eliminate. Following 5-FU treatment, a surviving population of 5-FU-resistant cells amounting to 4% of the initial population remained viable. When the surviving cell population from 5-FU-treated PANC-1 cells were exposed to alpha-gliadin peptide p31-43 (100 μg/mL or 200 μg/mL) for 7 additional days, cell proliferation was significantly suppressed. The ability of the gliadin peptide to effectively kill cells resistant to a potent chemotherapeutic agent such as 5-FU was surprising and unexpected.

Example 8

A549 cells were maintained and cultured as described in Example 4. Alpha-gliadin peptide p31-43 and cisplatin (Biovision, Milpitas, Calif.) were used to treat the cells. Cells (passage 32) were plated at a density of $1 \times 10^4$ cells/well in 24-well cell culture plates and allowed to adhere for 24 hours.

Cells were then incubated with vehicle (0.9% sodium chloride) or cisplatin at increasing concentrations for 72 hours. All experiments were conducted in triplicate. After incubation with cisplatin at concentrations ranging from 0 µM to 6.6 µM, cells were detached with trypsin and counted. Table 7 shows the mean cell number and percent growth inhibition following treatment with cisplatin.

TABLE 7

Anti-proliferative effects of cisplatin on A549 cells following 72-hour treatment

| Cisplatin Dose (µM) | Mean Cell | S.E. | % Inhibition | p-value |
|---|---|---|---|---|
| 0 (vehicle) | 193,017 | 3792 | — | — |
| 0.103 | 166,883 | 3217 | 13.5 | $p < 0.001$ |
| 0.207 | 150,917 | 2484 | 21.8 | $p < 0.001$ |
| 0.413 | 111,917 | 2146 | 42.0 | $p < 0.001$ |
| 0.825 | 48,400 | 3546 | 74.9 | $p < 0.001$ |
| 1.650 | 16,117 | 1762 | 91.6 | $p < 0.001$ |
| 3.300 | 10,033 | 452 | 94.8 | $p < 0.001$ |
| 3.600 | 3,222 | 136 | 98.3 | $p < 0.001$ |

Cells (passage 34) were then plated at a density of $5 \times 10^3$ cells/well in 24-well cell culture plates and allowed to adhere for 24 hours. Cells were incubated with the following: (1) vehicle (DMSO/water); (2) 3.3 µM cisplatin; (3) 70 µg/mL alpha-gliadin peptide p31-43; (4) 3.3 µM cisplatin and 70 µg/mL alpha-gliadin peptide p31-43 (high combination); or (5) 1.65 µM cisplatin and 35 µg/mL alpha-gliadin peptide p31-43 (low combination). All treatments were conducted in triplicate. For combination therapy using alpha-gliadin peptide p31-43 and cisplatin, the two compounds were administered to the cells simultaneously. Media was refreshed with the respective treatments every 72 hours. After 14 days of treatment, cells were trypsinized and counted. Table 8 shows the mean cell number and percent growth inhibition following treatment.

TABLE 8

Effects of cisplatin alone or in combination with alpha-gliadin peptide p31-43 on A549 cell proliferation following a 14-day treatment regimen

| Dose | Mean Cell Number/mL | S.E. | % Inhibition | p-value |
|---|---|---|---|---|
| 0 (vehicle) | 364,683 | 5334 | — | — |
| 3.3 µM cisplatin | 5,780 | 950 | 98 | $p < 0.001$ |
| 70 µg/mL gliadin | 325,217 | 1761 | 11 | $p > 0.05$ |
| 3.3 µM cisplatin + 70 µg/mL gliadin | 91,100 | 2350 | 75 | $p < 0.001$ |
| 1.65 µM cisplatin + 35 µg/mL gliadin | 132,783 | 1961 | 64 | $p < 0.001$ |

In order to examine the effects of alpha-gliadin peptide p31-43 on A549 cells exposed to cisplatin for an extended period of time (14 days), a second experiment was conducted on the surviving, i.e., resistant cell population (2%) from the previous experiment. Briefly, after counting viable cells on day 14 of treatment, the surviving cells were replated at a density of 5,000 cells per well. The following day, cells were treated with vehicle or 100 µg/mL or 200 µg/mL of alpha-gliadin peptide p31-43. Media containing the respective treatments was refreshed on day 3 and 6. On day 7, cells were trypsinized and counted. Table 9 shows the mean cell number and growth inhibition following treatment with alpha-gliadin peptide p31-43.

TABLE 9

Effects of alpha-gliadin peptide p31-43 on surviving cell population of cisplatin-resistant A549 cells

| Dose | Cell Number/mL | % Inhibition |
|---|---|---|
| Control | 2,600 | — |
| 100 µg/mL gliadin | 1,300 | 50% |
| 200 µg/mL gliadin | 900 | 65% |

The chemotherapeutic agent cisplatin, which damages DNA and is characterized as an alkylating agent, suppressed proliferation of A549 lung cancer cells. Cisplatin inhibited proliferation of A549 cells by 98% following treatment with 3.3 µM for 14 days. Co-administration of cisplatin and a gliadin peptide achieved significant growth inhibition compared to control cells. The results shown in Tables 3 and 8 suggested that the therapeutic efficacy of co-administering a gliadin peptide and a chemotherapeutic agent compared to either alone could be affected by the site of action (nucleus or cytoplasm) of the chemotherapeutic agent.

Surprisingly, administration of a gliadin peptide alone was effective in killing the cancer cells that prior treatment with cisplatin did not eliminate. Following cisplatin treatment, a surviving population of cisplatin-resistant cells amounting to 2% of the initial population remained viable. When the surviving cell population from cisplatin-treated A549 cells were exposed to alpha-gliadin peptide p31-43 (100 µg/mL or 200 µg/mL) for 7 additional days, cell proliferation was significantly suppressed. The ability of the gliadin peptide to effectively kill cells resistant to a potent chemotherapeutic agent such as cisplatin was surprising and unexpected.

Overall, the results in Examples 7 and 8 demonstrated that co-administering a gliadin peptide and a chemotherapeutic agent was effective in significantly inhibiting the growth of cancer cells. Surprisingly, administering a gliadin peptide alone achieved significant suppression of cancer cells that survived prolonged treatment with a potent chemotherapeutic agent. The surprising and unexpected ability of a gliadin peptide to advantageously and effectively kill the most resistant cancer cells, e.g., CSCs, indicated the gliadin peptide could be used in monotherapy or combination therapy to inhibit tumor growth and prevent cancer relapse. Administration of a gliadin peptide was therefore effective to decrease or prevent resistance of the cancer to the chemotherapeutic agent.

Example 9

The toxicity of alpha-gliadin peptide p31-43 in animals was evaluated. Five- to six-week old female BALB/c mice were dosed with vehicle (100 µL DMSO/saline) administered subcutaneously once a day for five days (Group 1) or 200 µg of alpha-gliadin peptide p31-43 in vehicle administered subcutaneously once a day for five days (Group 2). To prepare the gliadin solution, 70 µL of sterile DMSO was added to 1 mg of alpha-gliadin peptide p31-43 and vortexed to dissolve the peptide. After the peptide was dissolved, 430 µL of sterile 0.9% sodium chloride was added and vortexed to create a 1000 µg/500 µL solution of alpha-gliadin peptide p31-43.

Toxicity was evaluated using daily weight measurements and behavior assessments. The alpha-gliadin peptide p31-43 was associated with no treatment-related deaths. At the end of the study, the mean body weights (±SE) were 19.8±0.4 grams for Group 1 (n=5) and 20.0±0.3 grams for Group 2 (n=5). No behavior changes were observed in alpha-gliadin peptide p31-43 treated animals as compared to control mice. Alpha-gliadin peptide p31-43 was therefore tolerated at a dosing level of 10 mg/kg/day without apparent toxicity.

Example 10

The ability of alpha-gliadin p31-43 to induce apoptosis in cancer cells was assessed. A549 cells were maintained and cultured in RPMI 1640 media containing 10% fetal bovine serum, 2 mM L-glutamine and 1% antibiotic-antimycotic solution. Cells were grown in the presence of 5% $CO_2$ at 37° C. in an incubator. Induction of apoptosis following treatment with alpha-gliadin peptide p31-43 alone or in combination with gefitinib was determined using the terminal deoxynucleotidyl transferase dUTP nick-end labelling (TUNEL) assay.

Briefly, A549 cells ($1 \times 10^5$) were plated in chamber slides and allowed to adhere overnight. The cells were incubated for 72 hours with the following: (1) vehicle control; (2) 1 μM gefitinib; (3) 100 μg/mL, 200 μg/mL, or 500 μg/mL alpha-gliadin peptide p31-43; (4) 100 μg/mL, 200 μg/mL, or 500 μg/mL alpha-gliadin peptide p31-43 and 1 μM gefitinib. For combination therapy using alpha-gliadin peptide p31-43 and gefitinib, the two compounds were administered to the cells simultaneously. After the 72-hour treatment, the cells were fixed with 4% formaldehyde in PBS (pH 7.4) for 25 minutes at room temperature, then washed twice for 5 minutes in PBS, permeabilized in 0.2% Triton X-100 solution in PBS for 5 minutes at room temperature, and finally washed twice for 5 minutes in PBS. Apoptosis was measured using the DeadEnd™ Colorimetric TUNEL System (Promega, Madison, Wis.) according to the manufacturer's instructions. At the end of the assay, the cells were mounted and observed under the microscope. Staining of apoptotic cells was observed for cells treated with alpha-gliadin and/or gefitinib, and the percentage of cells that were apoptotic was determined by counting the number of stained cells within a representative sample. Table 10 shows the percent of cells that were apoptotic following each treatment and the p-value determined using one-way ANOVA analysis of the data for the gliadin- and gefitinib-treated cells compared to the control cells.

TABLE 10

Effect of gefitinib alone or in combination with alpha-gliadin peptide p31-43 on the induction of apoptosis

| Dose | Mean % apoptotic | S.E. | p-value |
|---|---|---|---|
| Control | 3 | 2 | — |
| gefitinib | 19 | 4 | $p > 0.05$ |
| 100 μg/mL gliadin | 37 | 7 | $p < 0.01$ |
| 200 μg/mL gliadin | 36 | 4 | $p < 0.01$ |
| 500 μg/mL gliadin | 38.5 | 1.5 | $p < 0.01$ |
| 100 μg/mL gliadin + gefitinib | 28.5 | 0.5 | $p < 0.05$ |
| 200 μg/mL gliadin + gefitinib | 37 | 1 | $p < 0.01$ |
| 500 μg/mL gliadin + gefitinib | 55 | 5 | $p < 0.001$ |

A significantly higher percentage of cells treated with alpha-gliadin peptide p31-43 alone were apoptotic, compared to cells treated with vehicle or gefitinib alone. Additionally, significantly more cells were apoptotic following combination therapy using alpha-gliadin peptide p31-43 and gefitinib, compared to cells treated with vehicle or gefitinib alone. The most effective treatment for inducing apoptosis was the combination of 500 μg/mL alpha-gliadin peptide p31-43 and gefitinib. Overall, the results demonstrated that alpha-gliadin peptide alone or in combination with gefitinib was a potent inducer of apoptosis in human lung cancer cells.

Example 11

The activity of gefitinib alone or in combination with alpha-gliadin peptide p31-43 was evaluated using an A549 human lung cancer xenograft model. Six-week old female nude mice (Harlan Laboratories, Indianapolis, Ind.) were quarantined for 3 days and housed 5 mice per cage, with a 12-hour light-dark cycle, and a relative humidity of 50%. Drinking water and diet were supplied to the animals ad libitum. All animals were housed under pathogen-free conditions. On day 4, $5 \times 10^6$ A549 cells in 100 μL of RPMI 1640 media were injected subcutaneously into the right flank of the mice. Starting 24 hours post-inoculation, animals were dosed once daily for 14 days as follows: Group 1—vehicle (2% DMSO in saline) administered intravenously; Group 2—150 mg/kg gefitinib administered by gavage; and Group 3—150 mg/kg gefitinib administered by gavage and 200 μg alpha-gliadin p31-43 administered intravenously. For combination therapy using alpha-gliadin peptide p31-43 and gefitinib, the two compounds were administered to the cells simultaneously. The animals were monitored for two weeks following the 14-day treatment period. Tumor measurements were initiated as soon as the tumor formed a palpable mass and measured twice weekly. Table 11 shows the mean body weights for the treatment groups over the course of the study.

TABLE 11

Effect of gefitinib alone or in combination with alpha-gliadin peptide p31-43 on body weight

| | Mean Body Weight (grams) | | | | | | | |
|---|---|---|---|---|---|---|---|---|
| | Dosing Period | | | | | Recovery Period | | |
| | Study Day: | | | | | | | |
| | 4 | 7 | 11 | 14 | 18 | 21 | 25 | 28 |
| Group 1 (control) | 18.52 ± 0.49 | 19.02 ± 0.90 | 19.40 ± 1.22 | 20.40 ± 1.18 | 20.92 ± 0.98 | 21.26 ± 0.89 | 22.34 ± 0.94 | 22.80 ± 0.88 |
| Group 2 (gefitinib) | 17.16 ± 0.42 | 17.28 ± 0.56 | 18.12 ± 0.78 | 18.78 ± 0.64 | 19.56 ± 0.58 | 21.12 ± 0.60 | 22.00 ± 0.52 | 22.50 ± 0.44 |

TABLE 11-continued

Effect of gefitinib alone or in combination with alpha-gliadin peptide p31-43 on body weight

| | Mean Body Weight (grams) | | | | | | | |
|---|---|---|---|---|---|---|---|---|
| | Dosing Period | | | | | Recovery Period | | |
| | Study Day: | | | | | | | |
| | 4 | 7 | 11 | 14 | 18 | 21 | 25 | 28 |
| Group 3 (gefitinib and gliadin) | 17.22 ± 0.40 | 17.88 ± 0.59 | 18.52 ± 0.45 | 19.00 ± 0.36 | 20.36 ± 0.42 | 21.70 ± 0.46 | 22.48 ± 0.42 | 22.92 ± 0.44 |

All treatments were well tolerated and associated with no drug-related deaths. No significant body weight loss was noted for any of the treatment groups. The mean body weights in grams (±S.E.) at termination were: Group 1=22.80±0.88, Group 2=22.50±0.44, and Group 3=22.92±0.44. Table 12 shows the mean tumor volumes for the treatment groups over the course of the study.

TABLE 12

Effect of gefitinib alone or in combination with alpha-gliadin peptide p31-43 on tumor volume

| | Mean Tumor Volume (mm$^3$) | | | | | | | |
|---|---|---|---|---|---|---|---|---|
| | Dosing Period | | | | | Recovery Period | | |
| | Study Day: | | | | | | | |
| | 4 | 7 | 11 | 14 | 18 | 21 | 25 | 28 |
| Group 1 (control) | 44.78 ± 6.48 | 60.44 ± 13.00 | 86.58 ± 15.44 | 118.60 ± 29.24 | 169.34 ± 40.87 | 227.86 ± 67.54 | 326.78 ± 91.72 | 402.86 ± 95.41 |
| Group 2 (gefitinib) | 47.74 ± 2.87 | 51.67 ± 5.69 | 49.30 ± 3.77 | 60.43 ± 5.35 | 75.40 ± 9.05 | 95.22 ± 11.15 | 157.69 ± 14.76 | 239.25 ± 32.78 |
| Group 3 (gefitinib and gliadin) | 27.24 ± 7.12 | 31.06 ± 8.13 | 40.89 ± 1.11 | 44.87 ± 3.13 | 50.12 ± 4.01 | 82.16 ± 8.72 | 112.79 ± 13.65 | 145.46 ± 19.74 |

At study termination day (Day 28), mean tumor volumes in cubic millimeters (±S.E.) were: Group 1=402.86±95.4, Group 2=239.25±32.78, and Group 3=145.46±19374. Table 13 shows the mean tumor volumes for the treatment groups over the course of the study.

TABLE 13

Effect of gefitinib alone or in combination with alpha-gliadin peptide p31-43 on tumor volume

| | Mean Percent Tumor Growth Inhibition | | | | | | | |
|---|---|---|---|---|---|---|---|---|
| | Dosing Period | | | | Recovery Period | | | |
| | Study Day: | | | | | | | |
| | 4 | 7 | 11 | 14 | 18 | 21 | 25 | 28 |
| Group 2 (gefitinib) | −6.61% | 14.51% | 43.06% | 49.05% | 55.48% | 58.21% | 51.74% | 40.61% |
| Group 3 (gefitinib and gliadin) | 39.18% | 48.61% | 52.77% | 62.16% | 70.40% | 63.94% | 65.48% | 63.89% |

The percent mean tumor growth inhibition values were 40.6% for Group 2 and 63.9% for Group 3. The tumor doubling times were 17.21 days for Group 1, 24.48 days for Group 2, and 22.89 days for Group 3. The tumor growth inhibition T/C ratio was 57.16 for Group 2 and 44.06 for Group 3.

Overall, the results demonstrated that combination therapy using gefitinib and a gliadin peptide produced a superior anticancer effect compared to gefitinib alone. The combination therapy was well-tolerated and not toxic to the animals, but was still effective at reducing the tumor burden. The mean tumor volume following combination therapy was reduced by more than 60% compared to control animals. The mean tumor volume was also significantly smaller (about 40%) following combination therapy compared to the mean tumor volume following treatment with gefitinib alone. Additionally, the combination therapy exhibited therapeutic efficacy significantly more rapidly than gefitinib alone, achieving close to 50% tumor growth inhibition within one week and maintaining greater than 60% growth inhibition for two weeks following cessation of treatment.

inhibit the growth of cancer cells, for a number of chemotherapeutic agents. Co-administration of a gliadin peptide with a RTKI resulted in greater therapeutic efficacy than the gliadin peptide or RTKI alone, and synergistic effects were surprisingly achieved. Despite exhibiting potent antitumor effects in vivo and the ability to dramatically reduce tumor volume and growth, administration of a gliadin peptide did not cause overall toxicity.

In view of the evidence described in the above Examples, the use of a gliadin peptide, alone or in combination with a chemotherapeutic agent, provides unexpected and surprisingly effective anticancer therapy.

While particular embodiments of the present invention have been illustrated and described, it would be obvious to those skilled in the art that various other changes and modifications can be made without departing from the spirit and scope of the invention. It is therefore intended to cover in the claims all such changes and modifications that are within the scope of this invention.

SEQUENCE LISTING

<160> NUMBER OF SEQ ID NOS: 3

<210> SEQ ID NO 1
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 1

Leu Gly Gln Gln Gln Pro Phe Pro Pro Gln Gln Pro Tyr
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 2

Pro Pro Gln Gln Pro Tyr
1               5

<210> SEQ ID NO 3
<211> LENGTH: 13
<212> TYPE: PRT
<213> ORGANISM: Homo sapiens

<400> SEQUENCE: 3

Pro Ser Gln Asp Ala Ser Leu Pro Pro Gln Gln Pro Tyr
1               5                   10

The foregoing Examples are provided to further illustrate the invention without being limiting. The data demonstrated that a gliadin peptide was an effective anticancer agent when used alone and was able to inhibit growth and induce apoptosis in drug-resistant cancer cells derived from a variety of different cancer types. A gliadin peptide administered alone was unexpectedly effective in killing even the most resistant cancer cells that survived prolonged treatment with a potent chemotherapeutic agent. Co-administration of a gliadin peptide and a chemotherapeutic agent was shown to significantly

What is claimed:

1. A method of treating cancer comprising administering a therapeutically effective amount of a gliadin peptide to a patient with cancer, wherein the gliadin peptide comprises the amino acid sequence set forth in SEQ ID NO:1 and is administered in a composition that does not contain an additional chemotherapeutic agent, wherein the cancer is non-small cell lung cancer.

2. The method of claim 1, further comprising co-administering a therapeutically effective amount of at least one chemotherapeutic agent.

3. The method of claim 2, wherein the at least one chemotherapeutic agent is a receptor tyrosine kinase inhibitor.

4. The method of claim 1, wherein the gliadin peptide is an alpha-gliadin peptide selected from the group consisting of alpha-gliadin peptide p31-55, p31-49, and derivatives and fragments thereof.

5. The method of claim 3, wherein the receptor tyrosine kinase inhibitor is an epidermal growth factor receptor (EGFR) inhibitor.

6. The method of claim 5, wherein the EGFR inhibitor is gefitinib.

7. The method of claim 5, wherein the EGFR inhibitor is erlotinib.

8. The method of claim 3, wherein co-administering the gliadin peptide and receptor tyrosine kinase inhibitor is effective to decrease or prevent resistance of the cancer to the receptor tyrosine kinase inhibitor.

9. The method of claim 1, wherein the patient is human.

10. The method of claim 5, wherein the patient does not have mutations in the EGFR gene known to increase sensitivity to EGFR inhibitors.

11. The method of claim 2, wherein co-administering the gliadin peptide and at least one chemotherapeutic agent is effective to decrease or prevent resistance of the cancer to the chemotherapeutic agent.

12. The method of claim 2, wherein co-administering the gliadin peptide and at least one chemotherapeutic agent is effective to increase the efficacy of the chemotherapeutic agent.

13. The method of claim 11, wherein the chemotherapeutic agent is administered first.

14. The method of claim 11, wherein the chemotherapeutic agent is selected from the group consisting of azacitidine, axathioprine, bevacizumab, bleomycin, capecitabine, carboplatin, chlorabucil, cisplatin, cyclophosphamide, cytarabine, daunorubicin, docetaxel, doxifluridine, doxorubicin, epirubicin, etoposide, fluorouracil, gemcitabine, trastuzumab, idarubicin, mechlorethamine, melphalan, mercaptopurine, methotrexate, mitoxantrone, oxaliplatin, paclitaxel, tafluposide, teniposide, tioguanine, retinoic acid, valrubicin, vinblastine, vincristine, vindesine, vinorelbine, and combinations thereof.

15. The method of claim 2, comprising administering the gliadin peptide via a route selected from the group consisting of oral, intramuscular, intravenous, respiratory/inhalation, and subcutaneous.

* * * * *